(12) United States Patent
Gao et al.

(10) Patent No.: US 6,551,497 B1
(45) Date of Patent: Apr. 22, 2003

(54) MEASURING NOX CONCENTRATION

(75) Inventors: Yunzhi Gao, Kumagaya (JP); Akira Kunimoto, Kumagaya (JP); Yongtie Yan, Kumagaya (JP); Hideyuki Kurosawa, Kumagaya (JP); Yukio Nakanouchi, Kumagaya (JP); Norio Miura, Fukuoka (JP); Noboru Yamazoe, Kasuga (JP); Masaharu Hasei, Kumagaya (JP)

(73) Assignee: Kabushiki Kaisha Riken, Tokyo (JP)

( * ) Notice: Subject to any disclaimer, the term of this patent is extended or adjusted under 35 U.S.C. 154(b) by 0 days.

(21) Appl. No.: 09/469,239

(22) Filed: Dec. 22, 1999

Related U.S. Application Data

(63) Continuation of application No. 09/068,742, filed as application No. PCT/JP97/03262 on Sep. 16, 1997, now abandoned.

(30) Foreign Application Priority Data

Sep. 17, 1996 (JP) .............................. 9-265061

(51) Int. Cl.[7] ............................................ G01N 27/407
(52) U.S. Cl. .................. 205/781; 204/425; 204/426; 204/427
(58) Field of Search .............. 204/421–429; 205/781, 783.5–785

(56) References Cited

U.S. PATENT DOCUMENTS

| 2,861,926 A | * | 11/1958 | Jacobson |
| 4,264,425 A | * | 4/1981 | Kimura et al. |
| 4,298,573 A | * | 11/1981 | Fujishiro |
| 4,582,657 A | * | 4/1986 | Shibata et al. |
| 4,657,659 A | * | 4/1987 | Mase et al. |
| 4,770,760 A | * | 9/1988 | Noda et al. |
| 5,080,775 A | * | 1/1992 | Yamachi et al. |
| 5,480,535 A | * | 1/1996 | Kondo et al. |
| 5,672,811 A | * | 9/1997 | Kato et al. |
| 5,736,028 A | * | 4/1998 | Hjortsberg et al. |

FOREIGN PATENT DOCUMENTS

| JP | 63-38154 A | 2/1988 |
| JP | 4-6459 A | 1/1992 |
| JP | 4-142455 A | 5/1992 |
| JP | 5-288710 A | 11/1993 |
| JP | 6-160324 A | 6/1994 |
| JP | 7-209249 A | 8/1995 |
| JP | 7-234203 A | 9/1995 |
| JP | 9-274011 A | 10/1997 |
| JP | 9-329578 A | 12/1997 |

OTHER PUBLICATIONS

Nobuhide Kato et al.; "Thick Film ZrO2 NOx Sensor"; SAE Technical Paper Ser. No. 960334; 1996 month available.

* cited by examiner

Primary Examiner—T. Tung
(74) Attorney, Agent, or Firm—Kubovcik & Kubovcik

(57) ABSTRACT

A gas sensor for measuring concentration of a gas component in a measured gas, including a solid electrolytic substrate and at least two electrodes fixed to the substrate. At least a first electrode of the electrodes is disposed in the environment of the measurement gas, at least one of electrodes is polarized by applying a bias current or bias voltage, and a change in the potential of the polarized electrode is measured to thereby measure the concentration of the target gas.

4 Claims, 10 Drawing Sheets

NO₂ CONCENTRATION (ppm)

NOx CONCENTRATION (ppm)

MEASURING NOX CONCENTRATION

This application is a continuation of application Ser. No. 09/068,742, filed May 15, 1998, now abandoned, which is a national stage application under 35 U.S.C. 371 of PCT/JP97/03262 filed Sep. 16, 1997.

BACKGROUND OF THE INVENTION

1. Field of the Invention

This invention relates to a gas sensor and, more particularly, to a gas sensor capable of being utilized as an NOx sensor for sensing the concentration of nitrogen oxides in combustion gas. The principle of the present invention is widely applicable to the sensing of gases other than nitrogen oxides as well.

2. Description of the Prior Art

Emissions of NOx from internal combustion engines used mainly in automotive vehicles and from the combustion equipment of thermal power stations and plants are a cause of photochemical smog and acid rain, are harmful to the human respiratory system and represent a major source of global environmental pollution. For these reasons the detection of noxious gases such as NOx is a major concern and a gas sensor that contributes to a reduction in the size and cost of measurement equipment and that is usable in a variety of environments has been sought.

In recent years much attention has been focused on all solid-state NOx sensors inserted directly into the exhaust gas of an automotive vehicle to sense the gases continuously, and results of related research have been reported. By way of example, a current-type sensor has been reported (see SAE Technical Paper 960334) as a sensor capable of sensing NOx concentration in the high-temperature exhaust gas of an automotive vehicle. This sensor has an ion conductor provided with two chambers. In the first chamber the concentration of oxygen in the measurement environment is made substantially zero and $NO_2$ is reduced to NO by an oxygen pump. A voltage is applied to electrodes provided in the second chamber to ionize the NO produced by reduction of the $NO_2$ as well as oxygen produced by the reduction of $NO_2$ to NO in the measurement environment. The resulting current is then detected to sense the concentration of NOx. Since an oxygen pump that reduces $NO_2$ to NO in order to detect the NOx concentration is employed in this sensor, the sensed NOx concentration varies greatly depending upon the performance of the oxygen pump and the concentration of residual oxygen and the individual concentrations of NO and $NO_2$ cannot be measured.

A semiconductor-type sensor utilizing the semiconductor properties of various oxides and exhibiting a varying electrical conductivity has been reported as an example of an NOx sensor. For example, Japanese Patent Laid-Open Publication NO. 6-160324 discloses a sensor using tin oxide as a gas-responsive element. However, since the sensitivity to NO gas and the sensitivity to $NO_2$ gas differ in this sensor, the concentration of NOx in a measurement environment in which NO and NOx coexist cannot be sensed.

Another arrangement is disclosed by the disclosures of Japanese Patent Laid-Open Publication No. 4-142455. This specification proposes a mixed potential-type NOx sensor having a sensing electrode and a reference electrode disposed in an ion conductor, wherein a potential difference across the electrodes is measured in gas undergoing measurement. Though this sensor is sensitive to both NO and $NO_2$, the sensitivities to NO and $NO_2$ are of opposite polarity. Consequently, outputs indicative of NO and $NO_2$ cancel each other out in a gas in which NO and $NO_2$ coexist and the concentration of NOx cannot be detected accurately as result. In other words, the overall NOx concentration cannot be sensed. In attempt to solve this problem, the inventors have proposed an overall NOx sensor (see the specifications of Japanese Patent Application Nos. 8-85419and 8-165105) in which a solid electrolyte of zirconia is provided with an internal cavity communicating with the measurement environment and NOx is separated into an NO or $NO_2$ gas component, which is then detected. This is a mixed potential-type overall NOx sensor in which one or two chambers are formed in the solid electrolyte of zirconia and NOx (the main components of which are NO and $NO_2$) is reduced to NO or oxidized to $NO_2$ by an electrochemical oxygen pump or by a catalyst in at least one of the chambers, after which the separated NOx component is sensed. However, it is obvious that in a case where the NOx is not completely separated into one of the gas components, NO and $NO_2$ will mix and interfere with each other. For example, if the performance of a catalytic converter for separating NOx into individual gas components deteriorates, this deterioration will cause a direct fluctuation in the sensor output.

Thus, in the gas sensors proposed heretofore, the oxidation of NO or the reduction of $NO_2$ is brought about using means such as a catalyst or an oxygen pump in order to sense the NOx concentration in a measurement environment. Either NO or $NO_2$ is sensed and adopted as the overall NOx concentration after the NOx contained in the environment is changed to either NO or $NO_2$. As a result, the concentrations of each of NO and $NO_2$ cannot be measured. In addition, the sensed concentration of NOx is highly dependent upon the performance of the catalyst or oxygen pump and it is difficult to detect the NOx concentration accurately.

Further, the mixed potential-type nitrogen oxide sensors measure the electrode potentials of the coexisting oxygen and nitrogen oxide gases using activated electrodes for oxygen and for one or both of NO and $NO_2$. However, the equilibrium potential of NO is negative and that of $NO_2$ is positive with respect to the electrode potential solely of the oxygen (air) electrode of the identical electrodes. Consequently, in a case where it is attempted to detect the sum of NO and $NO_2$ as NOx by identical electrodes, the mixed potential of the sensing electrode varies in the negative direction in conformity with the concentration of NO and in the positive direction in conformity with the concentration of $NO_2$. Accordingly, if NO and $NO_2$ coexist simultaneously, the changes in potential cancel each other out and it is difficult to reflect the concentration of NOx. Moreover, since the total change in potential becomes small, the sensor is readily susceptible to noise.

Thus, a mixed potential-type NOx sensor according to the prior art requires a highly active electrode material for the equilibrium of the sensing electrode, and the output signal is not always satisfactory. A mixed potential-type total NOx sensor also is disadvantageous in that a decline in NOx conversion performance has a direct adverse effect upon sensor output.

SUMMARY OF THE INVENTION

Accordingly, an object of the present invention is to provide a gas sensor useful for sensing NOx, wherein the sensor produces a stabilized output regardless of the state in which the nitrogen oxides exist and is not readily affected by variations in NOx conversion performance.

Another object of the present invention is to provide a sensor capable of sensing the concentrations of at least $NO_2$ and NO in a measurement environment so that the concentration of NOx can be sensed accurately.

A further object of the present invention is to provide a sensor in which variations in electrode potential caused by NO and $NO_2$ existing in a measurement gas are caused to occur in the same direction so that total NOx can be detected and the sensitivity of the sensor improved.

According to the present invention, the foregoing objects are attained by providing a gas sensor comprising: a solid electrolytic substrate; and at least two electrodes fixed to the substrate; wherein at least a first electrode of the electrodes is disposed in a gas environment to be detected, at least a second electrode of the electrodes is polarized by applying a bias current or bias voltage, and a change in potential of the polarized electrode is measured to thereby measure a gas component concentration in the gas to be detected.

The electrodes are provided with the functions of a sensing electrode, reference electrode and auxiliary electrode, but a single electrode may be provided with two or three of these functions.

In another aspect of the invention, the foregoing objects are attained by providing a nitrogen oxide sensor comprising: an ion-conductive solid electrolyte; an oxygen pumping electrode fixed to the solid electrolyte and active with respect to oxygen; an oxygen sensing electrode fixed to the solid electrolyte and active with respect to oxygen; an oxygen pumping electrode for measurement fixed to the solid electrolyte and active with respect to oxygen and NOx gas; and a reference electrode fixed to the solid electrolyte; wherein the oxygen pumping electrode and the oxygen sensing electrode are formed in a first chamber, the oxygen pumping electrode for measurement is formed in a second chamber, gas diffusing holes are provided between a measurement environment and the first chamber and between the first chamber and the second chamber, the concentration of a gas undergoing measurement supplied to the first and second chambers is held constant by controlling the oxygen pumping electrode by an electromotive force across the oxygen sensing electrode, a constant current is passed across the oxygen pumping electrode for measurement in the second chamber, and NOx concentration is detected by sensing a change in potential, across the reference electrode and oxygen pumping electrode for measurement, that is based upon a change in NO concentration and $NO_2$ concentration.

In accordance with the construction of the present invention, NOx concentrations in a measurement gas need not necessarily be converted to NO or $NO_2$ concentration. The NO and $NO_2$ concentrations are detected by the potential across the oxygen pumping electrode for measurement and the reference electrode, as a result of which NOx concentration can be measured. Furthermore, in a case where the potential responses of the oxygen pumping electrode for measurement and reference electrode with respect to the concentrations of NO and $NO_2$ differ, means for sensing $NO_2$ or NO concentration by a multi-purpose electrode is provided, whereby NO or $NO_2$ concentration in the measurement gas is detected. This makes it possible to measure NOx concentration.

Other features and advantages of the present invention will be apparent from the following description taken in conjunction with the accompanying drawings, in which like reference characters designate the same or similar parts throughout the figures thereof.

DESCRIPTION OF THE PREFERRED EMBODIMENTS

Figure 1:
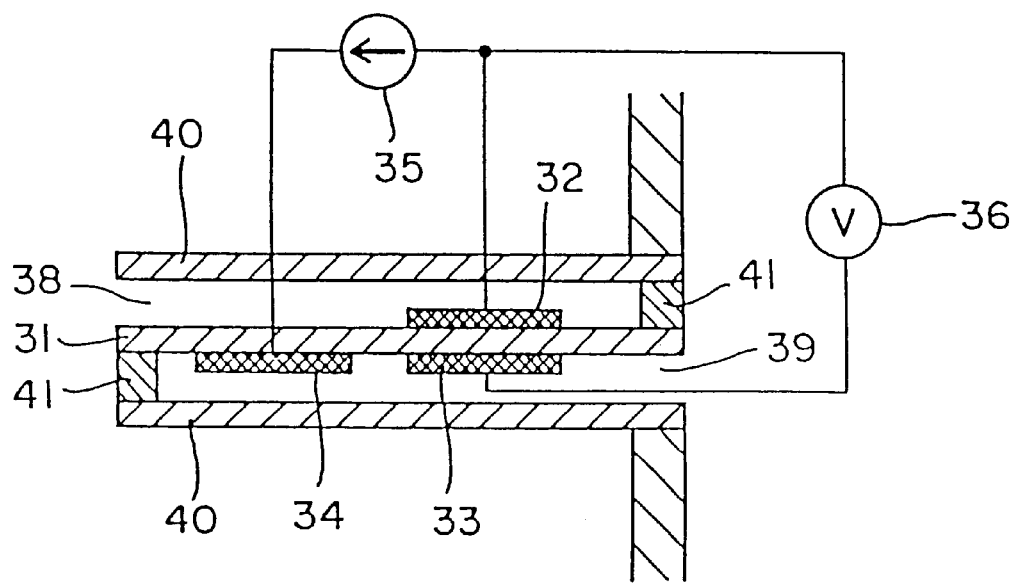
FIG. 1 is a sectional view illustrating a sensor according to a first embodiment of the present invention.

FIG. 1 illustrates the most basic embodiment of the present invention. A sensing electrode 32 serving as a first electrode active with respect to a gas to be detected at least in the polarized state, a reference electrode (e.g., a platinum electrode) 33 serving as a potentially stable second electrode inert or inactive with respect to the gas to be detected or not in contact with the gas to be detected, and an auxiliary electrode 34 serving as a third electrode for applying a bias are formed on an yttrium-stabilized solid electrolytic substrate of zirconia. It should be obvious that a sensor construction in which a solid electrolytic tube is used in place of the solid electrolytic substrate also falls within the scope of the present invention. The concentration of the gas undergoing measurement is sensed by measuring a change 36 in voltage across the first and second electrodes while a predetermined current 35 is passed between the first and third electrodes. Since the stability of the current source of the bias current plays a direct part in the stability of the sensor, it is preferred that a highly accurate and highly stable current source be used. Furthermore, the bias current value should be set in such a manner that a polarization potential falls between –0.3 and 0.4 V (exclusive of 0 V). On the other hand, with a view to reducing the influence of oxygen and raising the stability of the sensor to external noise, the potential of the sensing electrode 32 can be set between 0.4 and 1.2 V. By placing the auxiliary electrode 34 in the same space as that of the sensing electrode 32, a change in oxygen concentration caused by electric current can be reduced.

Figure 2:
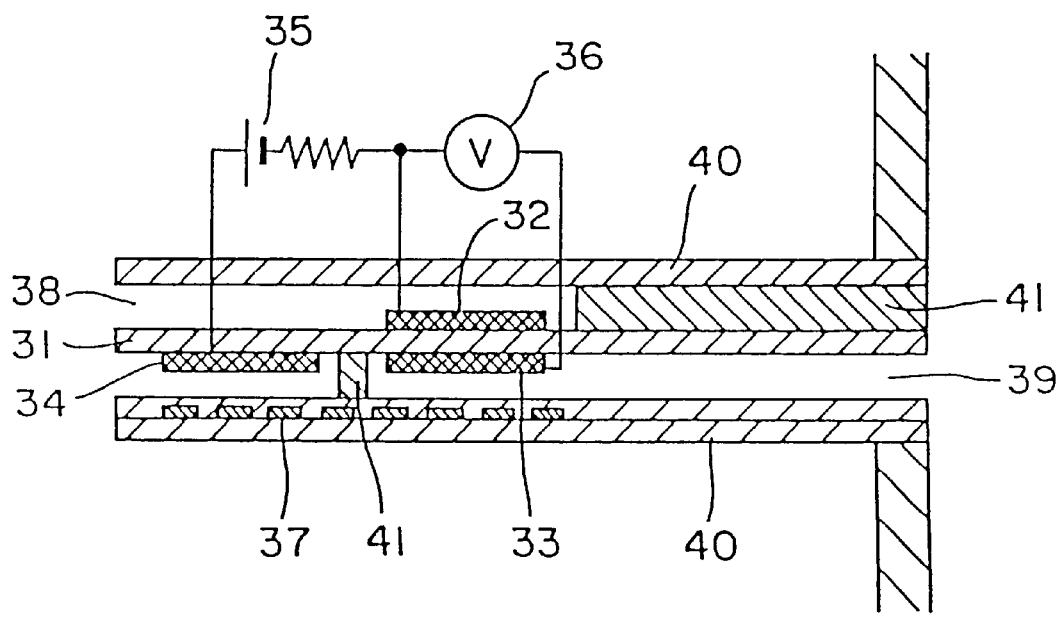
FIG. 2 is a sectional view in which a heater is disposed in the sensor of the first embodiment.

FIG. 2 is a sectional view showing a practical embodiment incorporating a heater 37 to provide the above embodiment with a self-heating function. The auxiliary electrode 34 is provided in a different space so that influence upon the sensing electrode can be eliminated.

A chamber 38 communicating with the gas environment to be detected and a chamber 39 communicating with the atmosphere are demarcated by a solid electrolytic substrate 31 and ceramic substrates 40, and ceramic spacers 41 are placed at suitable locations. The heater 37 is embedded in one of the ceramic substrates 40.

The solid electrolytic substrate need not necessarily be an yttrium-stabilized solid electrolytic substrate of zirconia but is at least required to be connected for ion current so that ions of the same type can be conducted. The sensing electrode or reference electrode is forcibly supplied with an externally applied current or voltage and it is required that the electrode be active at least to the target gas in a state in which the electrode is polarized electrochemically. In other words, the electrode need not be active to the target gas in a case where the electrode is not polarized. In order that the sensing electrode 32 or reference electrode 33 may be polarized, the auxiliary electrode 34 is a counter electrode for introducing current or voltage to the electrode that is to be polarized. Here the auxiliary electrode 34 must be connected to the polarized electrode via the solid electrolyte so as to pass an ion current. Upon measuring a potential difference due to electromotive force across the auxilliary electrode and the polarized sensing electrode 32 or reference electrode 33 in this basic arrangement having these electrodes and the solid electrolytic substrate 31, it was found that an output much larger than that produced with the simple mixed potential detection method of the prior art is obtained. Further, in a case where NO and $NO_2$ are detected, the sensor possesses exactly identical sensitivity polarities, irrespective of the type of NOx, entirely unlike the situation with the prior art. That is, in the prior art, the outputs relating to NO and $NO_2$ are oppositely directed and cancel each other out in an environment containing mixed gases. Neither NO nor $NO_2$ concentration can be sensed, let alone total NOx concentration. In accordance with the present invention, sensitivity is increased, the directions of the outputs are the same and there is almost no significant difference between the detection sensitivities. With NOx detection according to the present invention, therefore, overall NOx concentration can be detected with ease. It should be obvious that if the gas sensor based upon this sensing method is used, gases that can be detected are not limited to nitrogen oxides.

Figure 3:
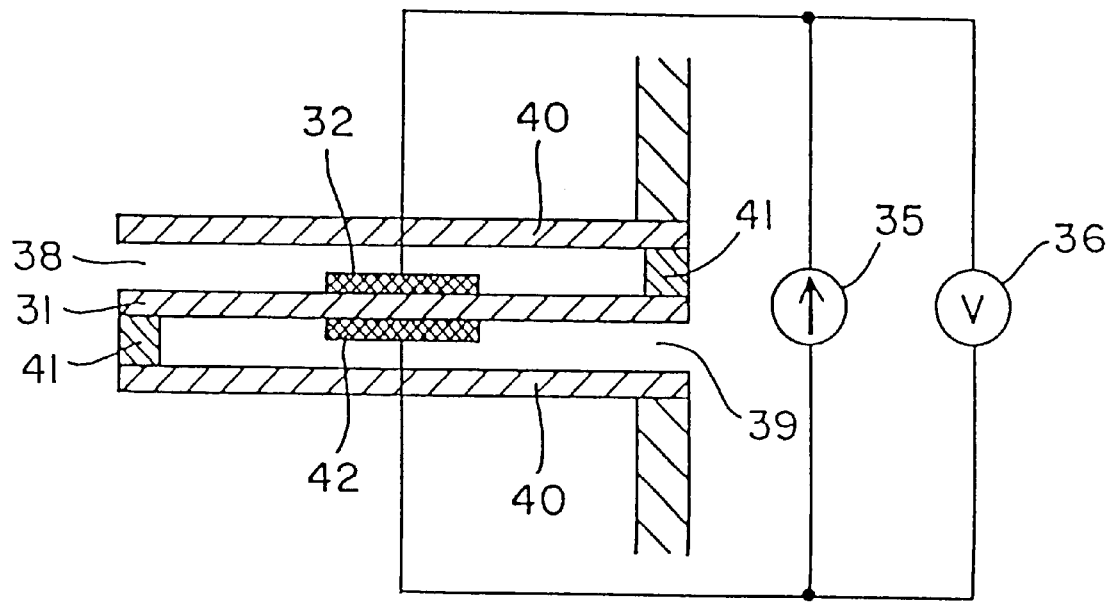
FIG. 3A is a sectional view illustrating a sensor according to a second embodiment of the present invention.
FIG. 3B is a sectional view showing a modification of the second embodiment of FIG. 3(a)
Figure 3:
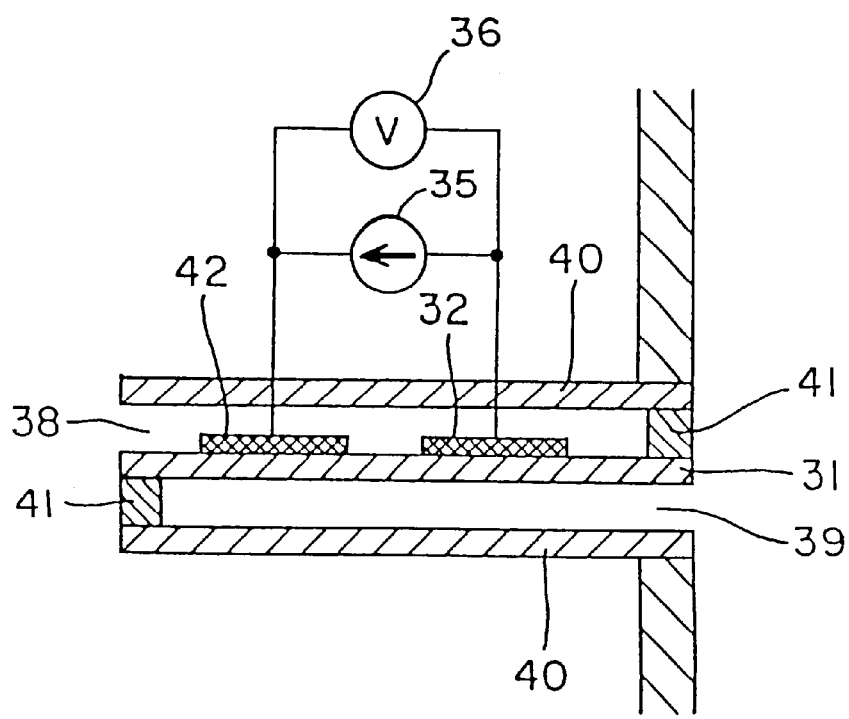

FIG. 3A is a sectional view illustrating an embodiment in which the structure of the gas sensor according to the present invention is simplified. As shown in FIG. 3A, the sensing electrode 32 serving as a first electrode active with respect to a gas to be detected at least in the polarized state and a dual-purpose electrode 42 serving as both a reference electrode and an auxiliary electrode potentially stable in the atmosphere are formed on the yttrium-stabilized solid electrolytic substrate 31 of zirconia. The concentration of the gas undergoing measurement is detected by measuring a change in voltage across the electrode 32 and the electrode 42 while a predetermined current 34 is passed between the electrode 32 and the electrode 42 using a constant-current source. It is preferred that the setting of the current or potential be carried out as mentioned earlier.

FIG. 3B is a sectional view of a modification in which the sensing electrode 32 and the dual-purpose electrode 42, which is inert to the target gas, are disposed in the chamber 38 communicating with the gas environment to be detected.

Figure 4:
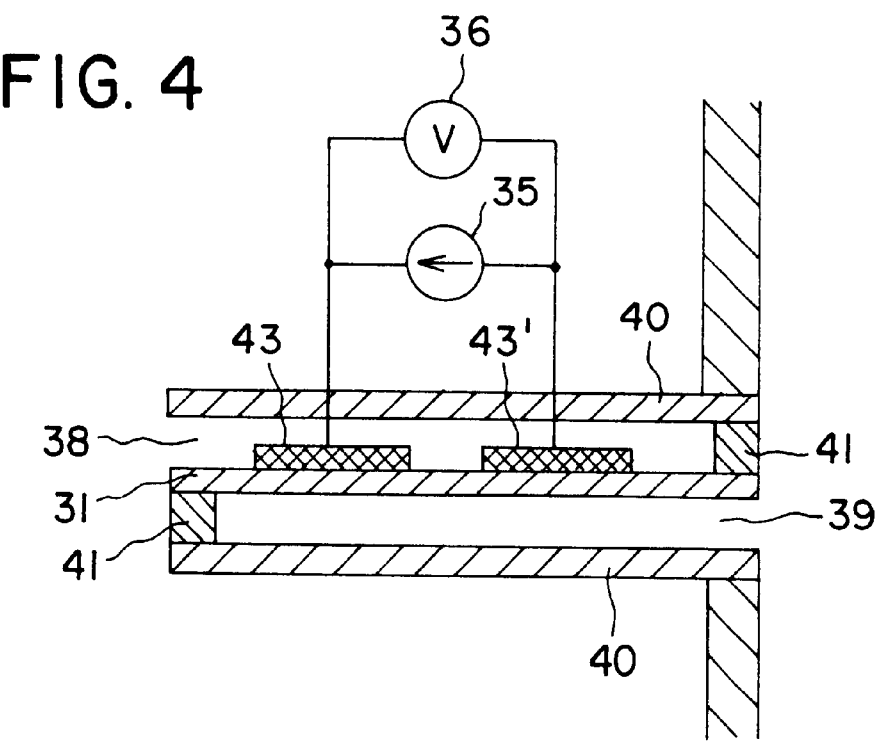
FIG. 4 is a sectional view illustrating a sensor according to a third embodiment of the present invention.

FIG. 4 illustrates an embodiment in which dual-purpose electrodes 43, 43', which function as a sensing electrode, reference electrode and auxiliary electrode, are fixed to the solid electrolytic substrate 31 so as to be disposed in the gas chamber 38.

If the bias current is adjusted to fall within ranges of 0.05~0.5 V and −0.03~−0.5 V for respective ones of the electrodes 43, 43', then the sensitivity of the sensor will be improved further owing to the fact that one electrode 43 will exhibit a response in a direction opposite that of the other electrode 43'. In addition, a change in the oxygen concentration at the surfaces of the electrode performing the sensing function and of the reference electrode serving as the counter electrode will be smaller than the change in oxygen concentration due to polarization owing to the oxidation and reduction reactions of oxygen at both electrodes.

Figure 5A:
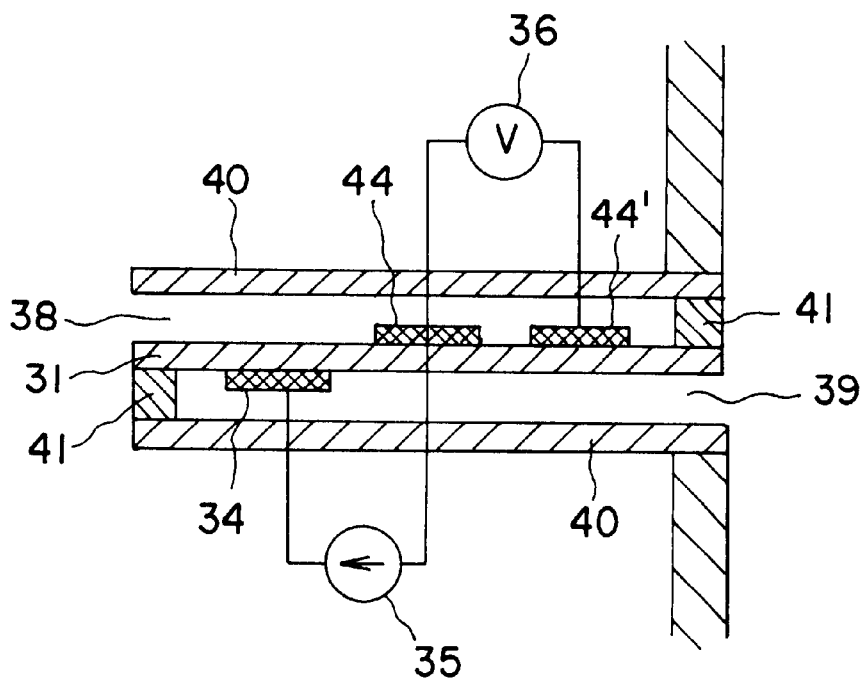
FIG. 5A is a sectional view illustrating a sensor according to a fourth embodiment of the present invention.

FIG. 5A is a sectional view illustrating another embodiment. Here multi-purpose electrodes 44, 44' performing the functions of both a sensing electrode and a reference electrode are fixed to the solid electrolytic substrate 31 on the side of the gas chamber 38 and in such a manner that the auxiliary electrode. 34 serving as the counter electrode is situated on the side of the gas chamber 39. By passing a prescribed bias current between the electrode 34 and the second electrode 44 disposed in close proximity to the first electrode 44' serving as the sensing electrode, the second electrode 44 serving as the reference electrode develops a potential response, which is contrary to that of the sensing electrode 44', to the gas to be detected. In addition, the oxygen ion potential in the electrolyte in the vicinity of the sensing electrode is caused to change. As a result, the sensitivity of the sensor is improved. More specifically, according to this embodiment, the sensing electrode 44' active to the type of gas to be detected is disposed on the solid electrolytic substrate 31 in an equilibrium state, and the reference electrode 44 active to NOx and its counter electrode 34 are disposed on the solid electrolytic substrate 31 in the polarized state, as shown in FIG. 5A. A change in the potential across the sensing electrode and reference electrode when at least the sensing electrode and reference electrode are exposed to the gas to be sensed is measured while passing a current between the reference electrode 44 and the auxiliary electrode 34 serving as the counter electrode. The sensing electrode and the reference electrode respond in positive and negative directions, respectively, and the sum of the absolute values of the outputs thereof is detected as the output of the sensor, thereby making it possible to obtain a sensor having a high sensitivity.

Figure 6:
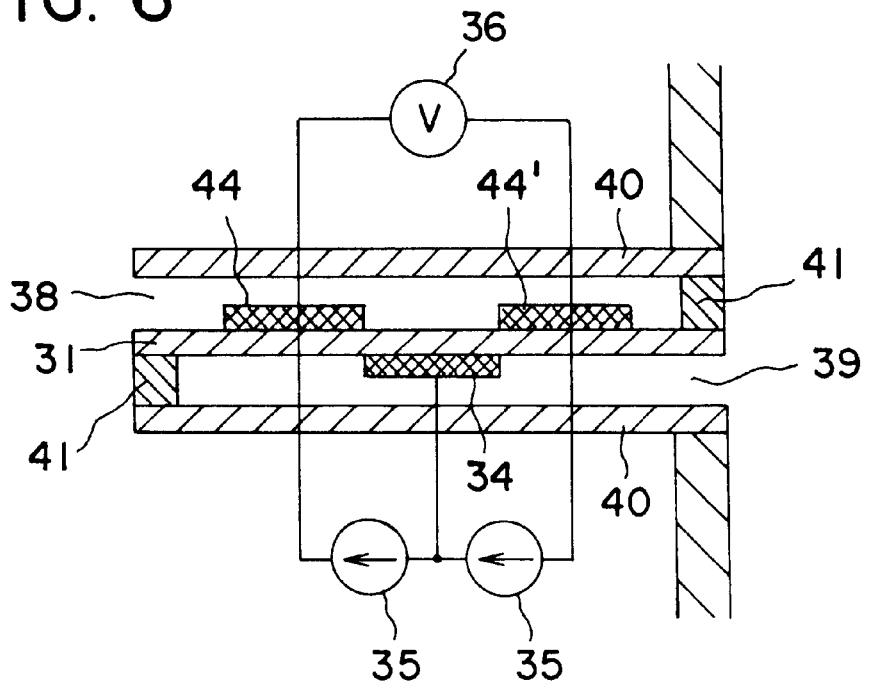
FIG. 6 is a sectional view illustrating a sensor according to a fifth embodiment of the present invention.

One more embodiment of the present invention will be described with reference to FIG. 6. In order to improve sensor output further and eliminate the influence of interfering gases, the first and second electrodes 44', 44 performing the functions of the sensing electrode and reference electrode can be polarized simultaneously using different currents. In the method described with reference to the second embodiment, a current is passed between the electrodes 32 and 42 and the contrary sensitivities at this time are sensed. However, the optimum states of polarization are not always obtained for these electrodes using identical currents. According to this embodiment, therefore, two current sources are used to achieve the optimum polarized states (in the same or opposite directions) of the electrodes 44, 44', and a change in the potential difference across the electrodes 44, 44' at this time due to NOx is measured, whereby the overall NOx concentration is detected. More specifically, one electrode 44 exhibiting activity to the target gas at least in the polarized state and the other electrode 44', which exhibits activity to the target gas of interest at least in the polarized state and is disposed in the same environment at that of the first-mentioned electrode 44, are fixed to the solid electrolytic substrate 31 having ion conductivity. These two electrodes 44 are polarized simultaneously by respective power supplies. The auxiliary electrode 34 serving as the counter electrode is placed on the side of the atmospheric chamber 39.

Figure 7:
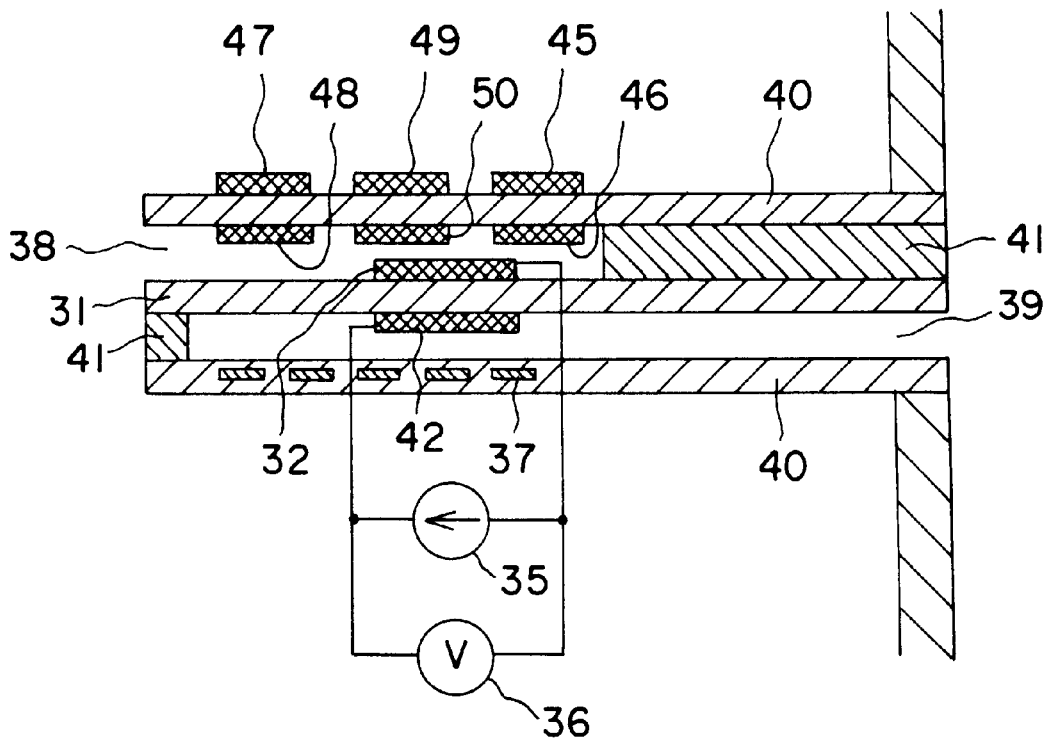
FIG. 7 is a sectional view illustrating a sensor according to a sixth embodiment of the present invention.

A practical embodiment of the present invention will now be described with reference to FIG. 7. Since the polarized electrode potential changes and NOx concentration cannot be detected accurately owing to oxidation or reduction of oxygen in the gas to be detected, it is required that the oxygen concentration be controlled so as to be rendered constant. Further, the catalytic function of the electrodes also varies depending upon a difference in electrode material, and a disparity in sensitivities to NO and $NO_2$ can be expected as well. Accordingly, it is desired that the oxygen concentration and the $NO:NO_2$ ratio in the gas to be detected be rendered constant to the maximum degree possible. A sensor construction taking this into consideration is illustrated in FIG. 7. An oxygen sensing electrode 46 and its counter electrode 45 are placed in the measurement chamber 18 and, via an electrolyte, on the side of the atmosphere, respectively, and oxygen pumping electrodes 48, 47 are formed respectively in the measurement chamber 18 and, via the electrolyte, external to the measurement chamber 18. The concentration of oxygen in the measurement chamber 18 is detected using the oxygen sensing electrode and the voltage applied to the oxygen pumps is adjusted based upon the electromotive force obtained, thereby varying the amount of intake or discharge of oxygen so that the oxygen concentration is controlled to a constant value. With regard to a disparity in sensitivities to NO and $NO_2$, an electrode 50, which is inert to oxygen, for converting NO to $NO_2$ or $NO_2$ to NO is placed in the measurement chamber 18 and its counter electrode 49 is placed outside the measurement chamber 18 via the intermediary of the electrolyte. Overall NOx is detected accurately by the sensing electrode after the oxygen concentration and $NO:NO_2$ ratio are thus rendered constant.

EXAMPLE 1

Figure 8:
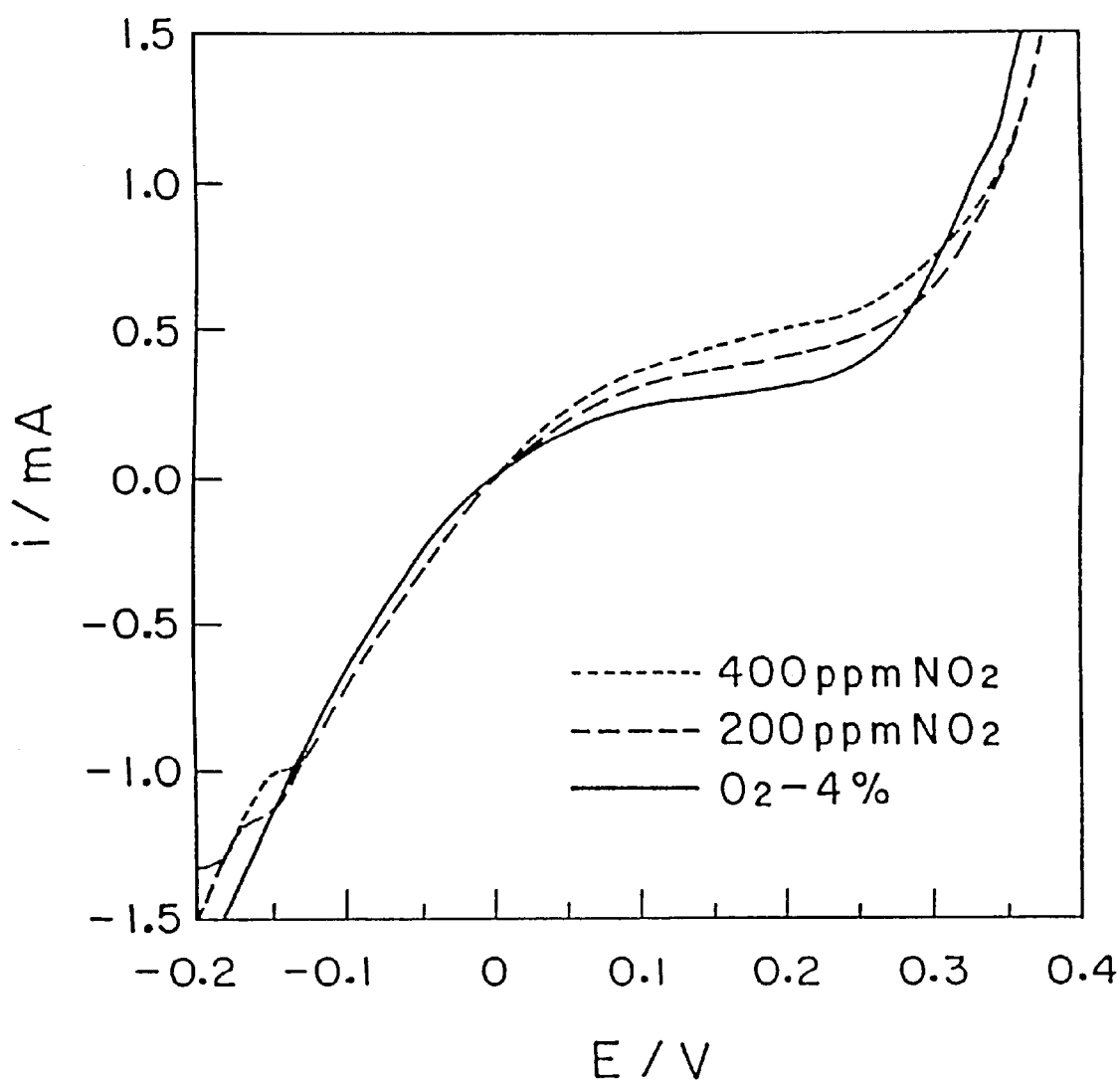
FIG. 8 is a diagram showing a current—potential curve of a platinum electrode according to the first embodiment.

A NOx sensor having a structure of the kind shown in FIG. 1 was fabricated by the following method to demonstrate the measurement principle of the present invention:

The sensing electrode 32, made of platinum, was formed on the upper surface of the solid electrolyte 31 exhibiting ion conductivity, and the reference electrode 33 and counter electrode 34 were formed on the side of the electrolyte 31 facing the atmosphere. The sensor was heated to 600° C. and, using a potentiostat, the polarization curves were measured in 4% oxygen having a nitrogen balance and following the addition of 200 ppm of $NO_2$ and 400 ppm of $NO_2$. The results are as shown in FIG. 8. An oxidation current dependent upon the concentration of $NO_2$ was clearly observed in a potential range of 0–0.3 V. In the absence of passed current, the platinum electrode exhibited absolutely no electrode potential response to $NO_2$. However, it was found that passing a constant current into the sensing electrode results in a large change in electrode potential. For example, when a constant current of 0.36 mA was passed into the sensing electrode and the concentration of $NO_2$ in gas containing 4% oxygen was made 0, 200 and 400 ppm in the order mentioned, it was verified that the electrode potential changed from 0.247 V to 0.163 V and from 0.163 V to 0.108 V in conformity with the change in $NO_2$ concentration.

EXAMPLE 2

An $NiCr_2O_4$ metal oxide electrode was fabricated on the upper surface of the solid electrolyte 31 of zirconia and was used as the sensing electrode 32, and the reference electrode 33, made of platinum, and the counter electrode 34 were formed on the opposite side of the solid electrolyte 31 to thereby fabricate a sensor having a structure of the kind shown in FIG. 1. A voltage was applied across the sensing electrode 32 and counter electrode 34 using a DC voltage-stabilized power supply in such a manner that the sensing electrode was rendered positive and the counter electrode negative. A high-impedance voltmeter 36 was connected across the sensing electrode 32 and reference electrode 33 to measure the potential. The sensor was heated to a temperature of 550° C. and 200 ppm of NO and 200 ppm of $NO_2$ were introduced as target gases to an air base. After the voltage applied across the sensing electrode 32 and counter electrode 34 was regulated to the predetermined values shown in Table 1 below, the potential of the sensing electrode was measured with respect to the reference electrode. The results obtained are as shown in Table 1.

TABLE 1

CHANGE IN POTENTIAL OF SENSING ELECTRODE DUE TO VOLTAGE APPLIED ACROSS SENSING AND COUNTER ELECTRODES

| | APPLIED VOLTAGE (mV) | | | |
|---|---|---|---|---|
| | 0 | 100 | 200 | 300 |
| $E_{Air}$ | 0 | 10.2 | 41 | 66 |
| $E_{NO}$ | −7.2 | 0.7 | 24.3 | 42.6 |
| $E_{NO_2}$ | 22.6 | 24.4 | 36.8 | 44.7 |
| $E_{NO}-E_{Air}$ | −7.2 | −9.5 | −16.7 | −23.5 |
| $E_{NO_2}-E_{Air}$ | 22.6 | 14.2 | −4.2 | −21.3 |

Though the potential of the sensing electrode in air varies owing to a change in applied voltage, a further change in electrode potential is brought about by the introduction of 200 ppm of NO and 200 ppm of $NO_2$. The value obtained by subtracting the potential value measured in the presence solely of air from the potential value measured in the presence of NO or $NO_2$ is the sensitivity, and it is evident that sensitivity varies in dependence upon the voltage applied across the sensing electrode 32 and counter electrode 34. For example, whereas sensitivities to NO and $NO_2$ at an applied voltage of 0 mV were −7 mV and 22.6 mV, respectively, the sensitivities obtained were −23.5 mV and −21.3 mV, respectively, when a voltage of 300 mV was applied across the sensing electrode and counter electrode. In other words, sensitivity to NO was raised and sensitivity to $NO_2$ could be changed from the positive to the negative direction. By utilizing this fact, responses in different directions for NO and $NO_2$ seen in the prior art can be made responses in the same direction. It is obvious that this is advantageous in terms of measuring total NOx.

EXAMPLE 3

Figure 5B:
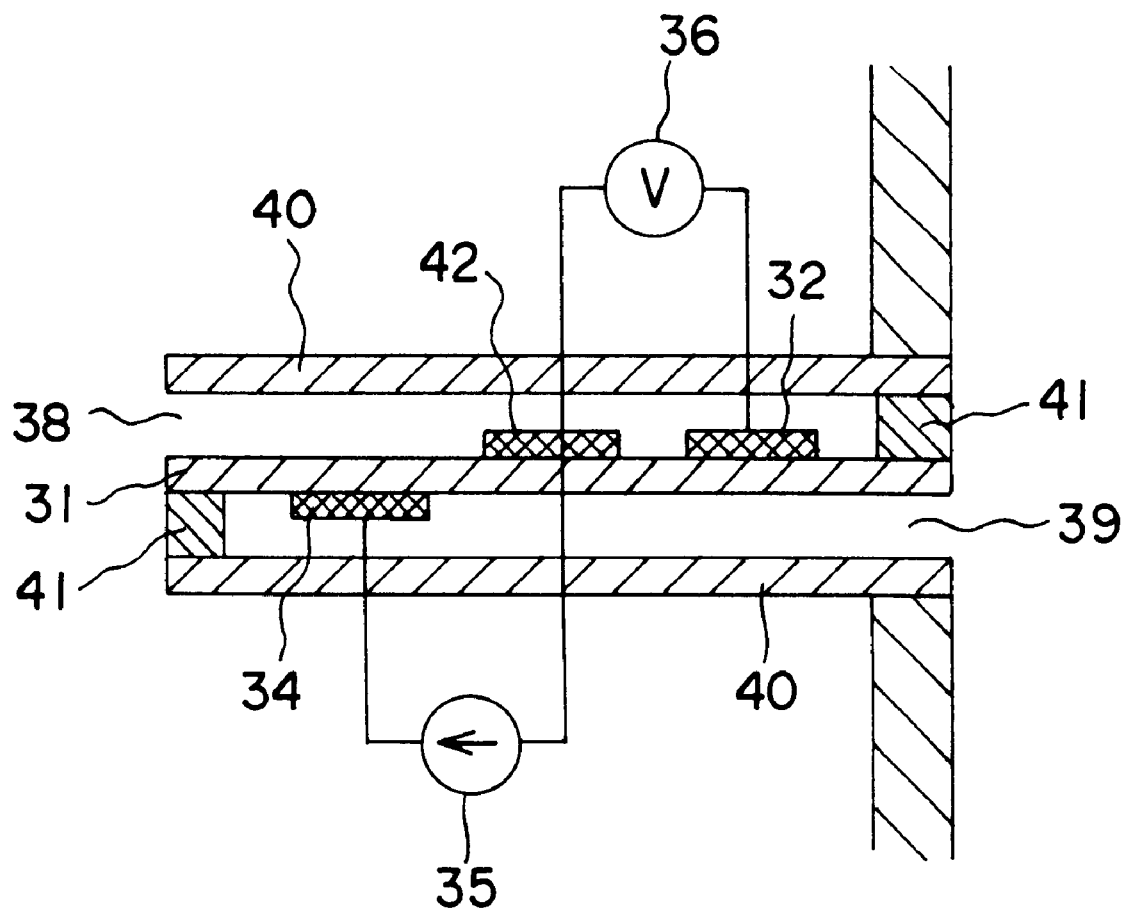
FIG. 5B is a sectional view illustrating the sensor described in Example 3.
Figure 9:
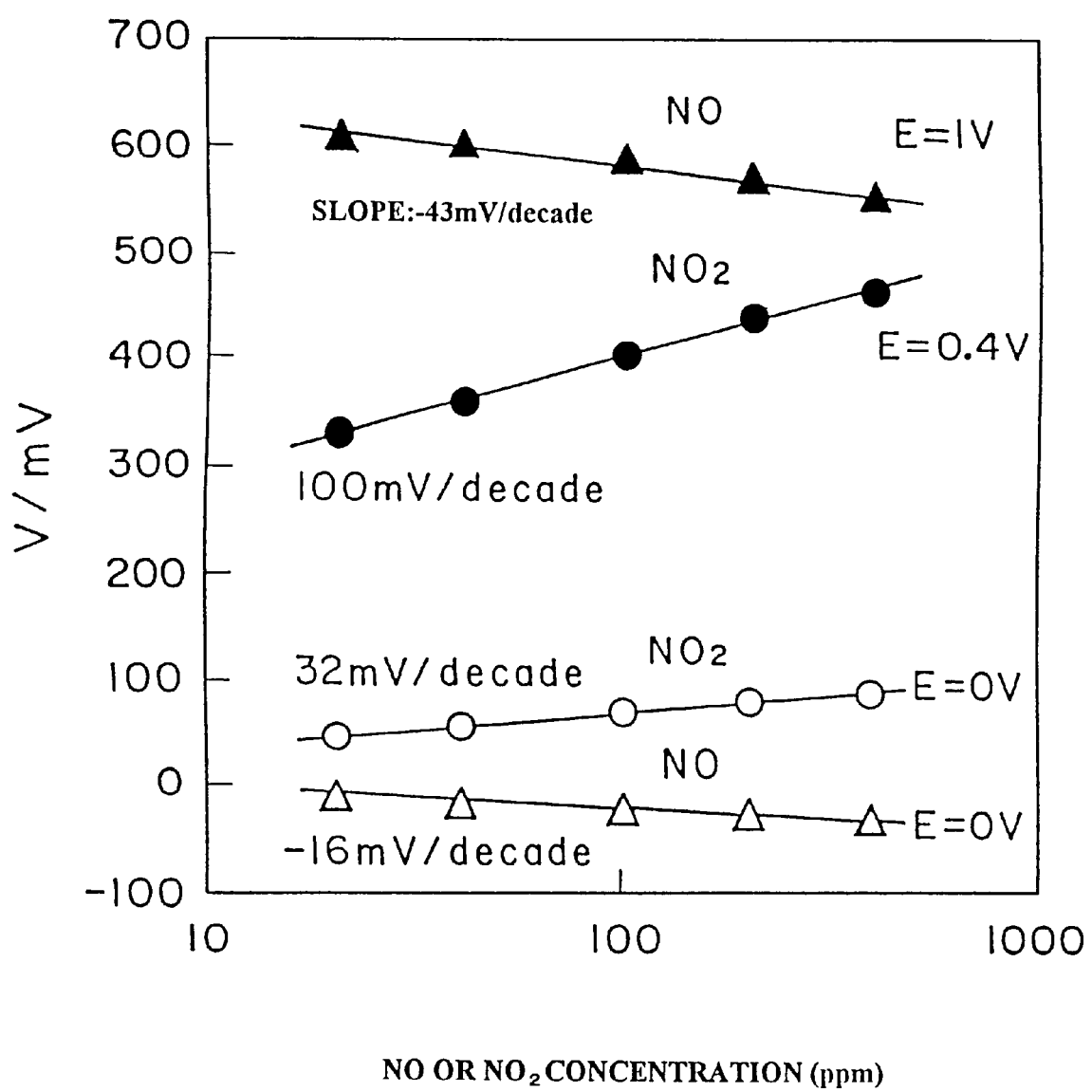
FIG. 9 is a diagram showing the dependence of a NOx sensor output on NOx concentration according to the fourth embodiment.

The sensing electrode 32, which consists of an electrode of Pt-Rh alloy, and the reference electrode 42, consisting of platinum, were disposed on the upper surface of the solid electrolyte 31 of zirconia, and the counter electrode 34 was formed on the opposite side of the electrolyte to fabricate the sensor having the structure shown in FIG. 5B. The sensor was heated to a temperature of 600° C., a predetermined voltage was applied across the counter electrode 34 and the reference electrode 42 to make the counter electrode positive and the reference electrode negative, NO gas or $NO_2$ gas was introduced at various concentrations to 4% oxygen, a predetermined voltage was applied across the electrode 42 and the electrode 32 via an electric resistance using a stabilized power supply, and a change in the potential difference across the electrodes 42, 32 was measured. The results obtained are as shown in FIG. 9. It was verified from these results that sensitivities to NO and $NO_2$, as well as the slopes thereof, in the polarized state (E=0.4 V, E=1 V) were greatly increased in comparison with the values that prevailed in the equilibrium state (E=0 V) prior to polarization. Though the sensitivities to NO and $NO_2$ differ, it is possible to eliminate this problem if the gas is separated into individual gas components by a gas converter with which the sensor is additionally provided.

EXAMPLE 4

Figure 10:
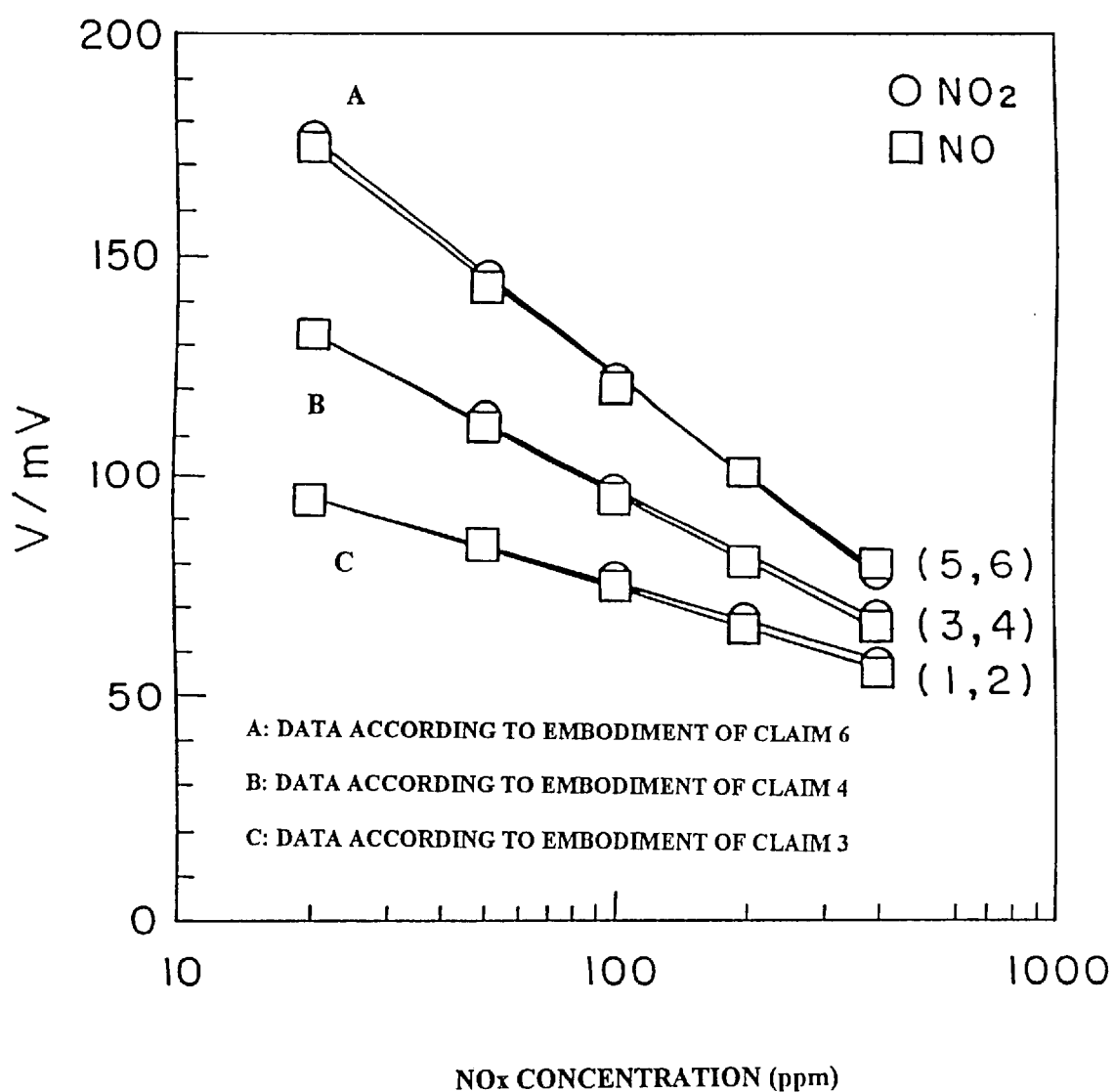
FIG. 10 is a diagram showing the dependence of a NOx sensor output on NOx concentration according to the fourth embodiment.

A sensing electrode was obtained by fabricating an electrode of Pt-Rh alloy on the upper surface of the solid electrolyte of zirconia, and a reference electrode, consisting of platinum, was formed on the opposite side of the electrolyte to fabricate the sensor having the structure shown in FIG. 3A. The sensor was heated to a temperature of 550° C. and a constant current of 0.1 $\mu A$ as passed between the sensing electrode and reference electrode to make the sensing electrode positive and the counter electrode negative, thereby polarizing the sensing electrode. Next, NO gas or $NO_2$ gas was introduced at various concentrations to 4% oxygen and a change in the output of the sensor was measured. The results obtained are as shown in FIG. 10 (see the straight lines 1, 2). Further, a Pt-Rh alloy electrode and a platinum reference electrode were formed on the same surface on the side in contact with the gas to be sensed to fabricate an NOx sensor having the structure shown in FIG. 4, and the change in the output of the sensor was measured under conditions similar to those mentioned above. The results obtained are shown in FIG. 10 (see straight lines 3, 4). Furthermore, an NOx sensor having the structure shown in FIG. 6 was fabricated, currents of 0.1 $\mu A$ and –0.3 $\mu A$ were passed through the electrodes 44 and 34, respectively, and the change in the output of the sensor was measured under temperature, oxygen concentration and NOx concentration conditions similar to those mentioned earlier. The results obtained are shown in FIG. 10 (see straight lines 5, 6). These results demonstrate that this sensor exhibits substantially the same sensitivity to NO and $NO_2$ and that the slopes of the sensitivity curves are increased.

It should be noted that Pt-Rh can be used as the sensing electrodes and that Pt may be used as the reference electrode and as the auxiliary electrode serving as the counter electrode. One of the dual-purpose electrodes may consist of Pt-Rh and the other may consist of $Cr_2O_3$.

Further embodiments of a NOx sensor according to the present invention will be described with reference to FIGS. 11 and 12.

Figure 11:
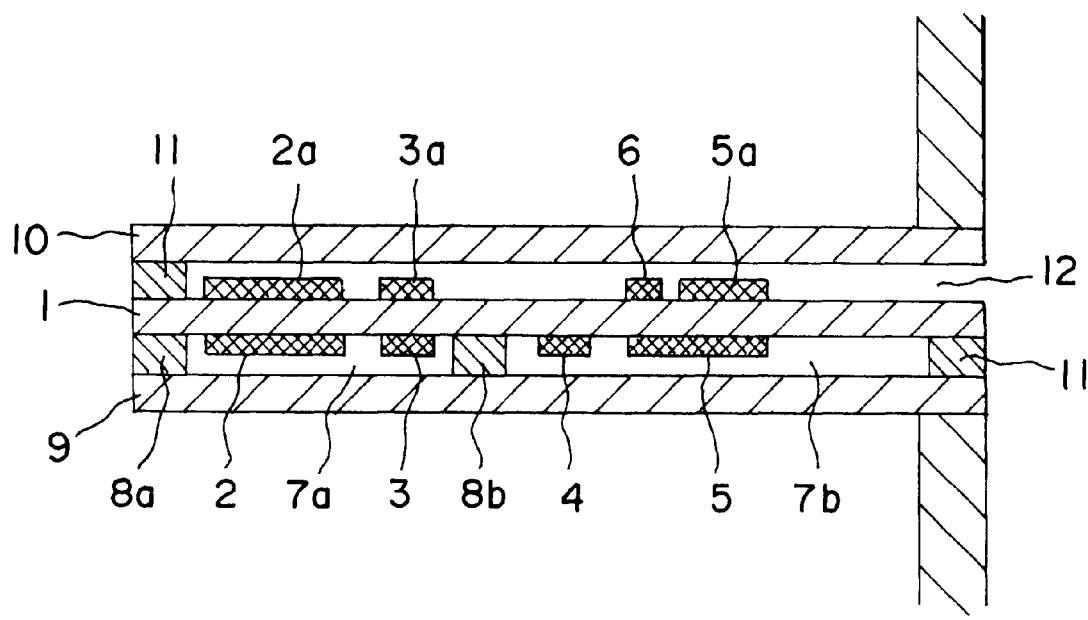
FIG. 11 is a sectional view illustrating a nitrogen oxide sensor according to the present invention.

FIG. 11 illustrates a developmental arrangement of a NOx sensor according to the present invention. The NOx sensor comprises an ion-conductive solid electrolyte 1; an oxygen exhausting electrode 2 fixed to the solid electrolyte 1 and active to oxygen; an oxygen sensing electrode 3 fixed to the solid electrolyte 1 and active to oxygen; a composite sensing electrode 4 fixed to the solid electrolyte 1 and active to oxygen and $NO_2$ gas; an oxygen exhausting electrode 5 for measurement fixed to the solid electrolyte and active to oxygen and NOx gas; and a reference electrode 6 fixed to the solid electrolyte. The oxygen exhausting electrode 2 and the oxygen sensing electrode 3 are formed in a first chamber 7a and the composite sensing electrode 4 and the oxygen exhausting electrode 5 for measurement are formed in a second chamber 7b. The first chamber 7a and the second chamber 7b, are covered by ceramic spacers 11 and a ceramic substrate 9, and gas diffusing holes 8a, 8b are formed between the measurement environment and the first chamber and between the first chamber and the second chamber, respectively. The basic construction of the arrangement of FIG. 11 corresponds to FIG. 1.

It is preferred that the oxygen exhausting electrode 2 consist of a material active solely to oxygen. Further, the first chamber 7a has a space enough to exhaust oxygen to render the partial pressure of oxygen in the first chamber 7a constant under such a voltage that an NO or $NO_2$ reductive reaction will not be caused by the electrode to which the voltage is applied, even if the electrode is active to NO or $NO_2$. The other electrode 2a is covered by the ceramic spacer 11 and ceramic substrate 10 so that it will not come into contact with the measurement environment. The electrode 2a is placed at a position at which it will contact the atmospheric air via an opening 12 at one end of the sensor. The oxygen sensing electrode 3 is formed in the first chamber 7a, and the other electrode 3a is formed at a position at which it will contact the atmospheric air. The composite sensing electrode 4 is formed from an oxide of a transition metal that is active to oxygen and $NO_2$, and the collector consists of platinum. The reference electrode 6, which opposes the oxygen exhausting electrode 5 for measurement formed in the second chamber 7b, serves also as the counter electrode of the composite sensing electrode 4. The oxygen exhausting electrode 5 for measurement is formed in the second chamber 7b and consists of platinum. The counter electrode 5a of the oxygen exhausting electrode 5 for measurement consists of platinum and is formed at a position at which it will come into contact with the atmosphere. Similarly, the reference electrode 6 consists of platinum and is formed at a position at which it will come into contact with the atmospheric air.

The ion conductor 1 is an oxygen ion conductor and can be a solid electrolyte, which is obtained by adding a stabilizer to an oxide such as hafnium oxide, zirconium oxide or thorium oxide, or bismuth oxide. In terms of thermal and chemical stability, stabilized zirconia using a stabilizer such as yttrium oxide, magnesium oxide or calcium oxide is preferred. The gas to be measured flows into the first chamber 7a via the diffusing hole 8a and flows into the second chamber 7b via the diffusing hole 8b. The diffusing holes may be singular or plural of very small diameter. Porous bodies may also be used.

At least the oxygen in the measurement gas that has penetrated the first chamber 7a is exhausted by the oxygen exhausting electrode 2 and it will suffice if the arrangement is such that the partial pressure of oxygen in the first chamber 7a is rendered constant. Furthermore, the partial pressure of oxygen in the first chamber 7a is detected by the oxygen sensing electrode 3 formed in the first chamber 7a, and means is provided for controlling the voltage of the oxygen exhausting electrode 2 in such a manner that the partial pressure of oxygen in the first chamber 7a is rendered constant. In this case the oxygen exhausting electrode maybe formed in the second chamber 7b.

The measurement gas whose partial oxygen pressure has been rendered constant in first chamber 7a flows into the second chamber 7b so that the NO or $NO_2$ concentration will be detected by the composite sensing electrode 4 provided in the second chamber. The concentration of NO or $NO_2$ is detected as a potential difference with respect to the reference electrode 6. Furthermore, a voltage is impressed across the oxygen exhausting electrode 5 for measurement, which is provided in the second chamber 7b, and its counter electrode 5a in such a manner that a constant current will flow. The potential across the oxygen exhausting electrode 5 for measurement and the reference electrode 6 is measured. The constant current value established across the oxygen exhausting electrode 5 for measurement and its counter electrode falls at least within a range of current values and voltage values such that a limit current value will not be reached on the current-potential curve for oxygen in the second chamber. The current value is set to obtain a satisfactory voltage value that will bring about a NO and $NO_2$ reduction reaction. Since the reference electrode 6 is in contact with the atmospheric air whose oxygen concentration is constant, the potential thereof is fixed.

The oxygen exhausting electrode 5 for measurement is active with respect to oxygen and NOx and its potential is dependent upon the concentrations of NO and $NO_2$ in the second chamber 7b where the oxygen concentration is constant. If the change in potential for NO concentration is the same as that for $NO_2$ concentration, the concentration of NOx in the measurement environment can be detected without using the composite sensing electrode 4. If it is desired to detect the concentration of either NO or $NO_2$ or if the change in potential between the oxygen exhausting electrode 5 for measurement and the reference electrode 6 is not the same for NO and $NO_2$, then the concentrations of NO and $NO_2$ in the measurement gas can be detected from the concentration of NO or $NO_2$ sensed by the composite sensing electrode 4 and the potentials of the oxygen exhausting electrode 5 for measurement and reference electrode 6 based upon the concentrations of NO and $NO_2$. This makes it possible to detect the NOx concentration.

Figure 12:
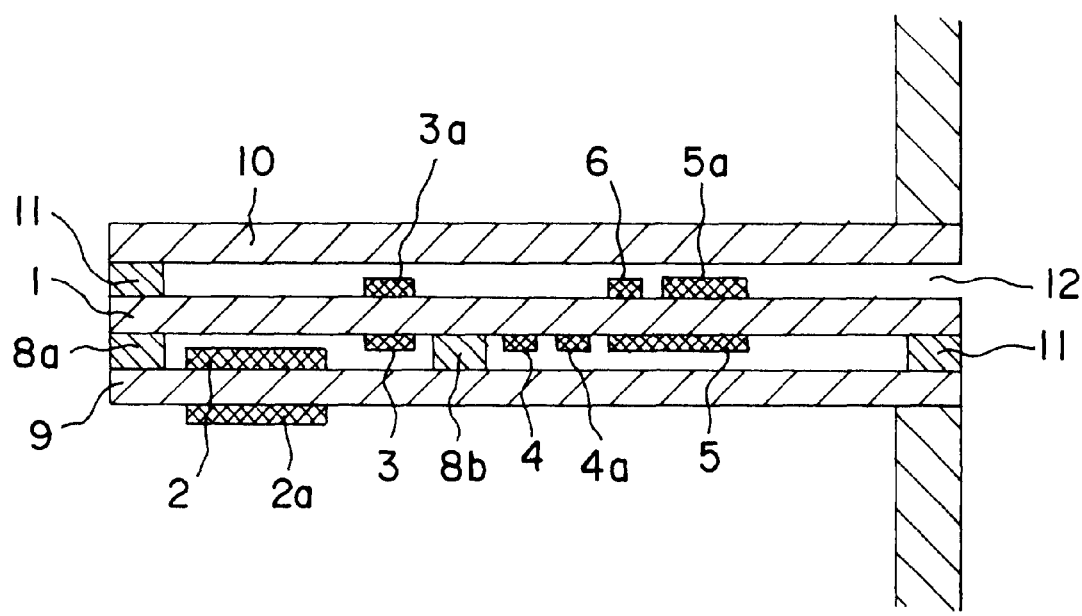
FIG. 12 is a sectional view showing another nitrogen oxide sensor according to the present invention.

In another method according to the present invention, as shown in FIG. 12, the ceramic substrate 9 covering the first chamber 7a and the second chamber 7b may consist of a material the same as that of the ion conductive solid electrolyte 1, and the oxygen exhausting electrode 2 and its counter electrode 2a or the composite sensing electrode 4 and its counter electrode may be formed on the ion conductive solid electrolytic substrate 1 without giving rise to any problems in terms of the operation of the sensor according to the present invention. It is required that the NOx sensor of the present invention be heated to a prescribed temperature because the sensor uses a solid electrolyte. However, heating may be derived from a high-temperature exhaust gas or the sensor may be heated to the prescribed temperature by provision of self-heating means. Heating by the self-heating means is especially preferred in order to obtain stabilized performance. For example, a heater for self-heating purposes may be formed directly on the ceramic substrate 9, or a substrate made of a ceramic or the like and having the heater embedded within it may be laid upon and affixed to the ceramic substrate 9. In the structure illustrated in FIG. 11, a self-heating device can be laid upon and affixed to the ceramic substrate 10.

EXAMPLE 5

The NOx sensor shown in FIG. 11 was fabricated and its performance was evaluated by the following method:

An 8 mol % yttrium-stabilized substrate 1 of zirconia having dimensions of 4×50×0.2 mm was used. The leads of the electrodes were formed on the zirconia substrate 1 by screen printing using platinum paste to which frit glass had been added, and the leads thus formed were fired. Platinum wires were then welded in place to obtain the lead wires. A film of $Cr_2O_3$ was then formed on the zirconia substrate 1 by sputtering and platinum was affixed to the film to form the composite sensing electrode 4. The oxygen exhausting electrode 2, oxygen sensing electrode 3, oxygen exhausting electrode 5 for measurement, reference electrode 6 and the counter electrodes 2a, 3a, 5a of these electrodes were formed by screen printing using finely powdered platinum paste not containing frit glass. The electrodes formed were then fired. It should be noted that the counter electrode of the composite sensing electrode is not the reference electrode shown in FIG. 11 but the structure of FIG. 12 newly provided in the second chamber 7b. Furthermore, the zirconia substrate 1 and the ceramic substrates 9, 10 were affixed, with the ceramic spacers 11 and diffusing holes 8a, 8b disposed between them, using glass of a high melting point. A ceramic substrate having an embedded heater was affixed to the ceramic substrate 9 by glass.

Figure 13:
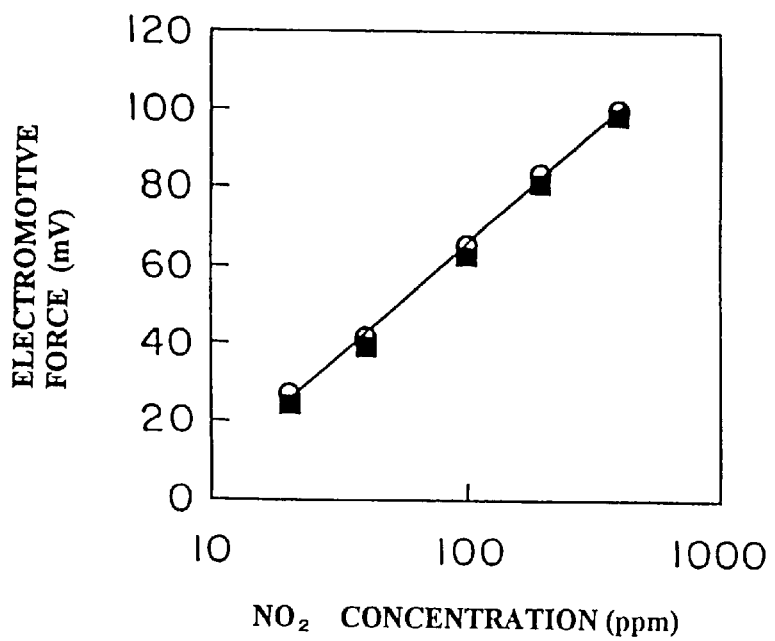
FIG. 13 is a diagram showing the dependence of the electromotive force of a multi-purpose sensing electrode on $NO_2$ concentration.

FIG. 13 illustrates the relationship between $NO_2$ concentration and electromotive force across the composite sensing electrodes when the oxygen exhausting electrode 2 was and was not made to operate in various measurement gases in which the sensor temperature was set to 600° C. The white circles indicate the relationship between $NO_2$ concentration and the electromotive force across the composite sensing electrodes in a case where the concentration of oxygen in the measurement gases was held constant at 0.1%. The black squares indicate the relationship between $NO_2$ concentration and the electromotive force across the composite sensing electrodes in a case where 100 ppm of NO coexisted with the $NO_2$ under these conditions. FIG. 13 indicates a change in electromotive force, with respect to $NO_2$ concentration, almost the same as that observed in the case where the oxygen exhausting electrode was not made to operate, even though the concentration of oxygen in the first chamber was controlled by operating the oxygen exhausting electrode and oxygen sensing electrode. A change in electromotive force proportional to the log of the $NO_2$ concentration was obtained. Further, the same dependence of electromotive force on $NO_2$ concentration was obtained in the case where 100 ppm of NO was made to coexist with $NO_2$. Thus it was confirmed that the concentration of $NO_2$ could be sensed by the sensing electrode regardless of whether or not the oxygen exhausting electrode was made to operate and whether or not NO coexisted with $NO_2$. The relationship between $NO_2$ concentration and electromotive force in this case is expressed by the following equation:

$$\text{electromotive force (EMF)} = 57.63 \log [NO_2 \text{ concentration (ppm)}] - 49.37 \qquad (1)$$

Figure 14:
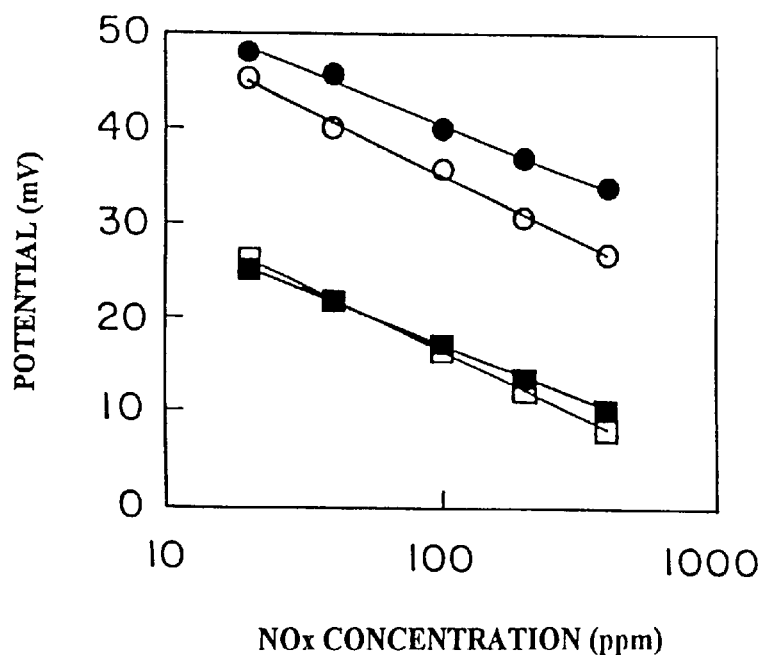
FIG. 14 is a diagram showing the dependence of potential across an oxygen pumping electrode and a reference electrode on NOx concentration.

FIG. 14 illustrates the relationship between $NO_2$ concentration and the potential across the oxygen exhausting electrode 5 for measurement and the reference electrode 6 when the oxygen exhausting electrode 2 and oxygen sensing electrode 3 were made to operate in a measurement gas having an oxygen concentration of 0.5% under a temperature of 600° C. to control the oxygen concentration in the first chamber to 0.1%, and a voltage was impressed across the oxygen exhausting electrodes 5, 5a to obtain a current flow of 0.05 mA. The white circle marks indicate a case in which the NOx contained in the measurement gas was $NO_2$ alone, the black circle marks a case in which the NOx contained in the measurement gas was NO alone, the white squares a case where the NO contained in the gas had a constant concentration (50 ppm), and the black squares a case where the NO$_2$ contained in the gas had a constant concentration (50 ppm). The change in potential across the electrodes is proportional to the log of the NO, NO$_2$ concentrations. Further, FIG. 14 indicates a potential change that is proportional to the log of the NO$_2$ or NO concentration even if a constant amount of NO or NO$_2$ coexists. On the basis of these results, the relationship between NOx concentration and potential can be expressed by the following equation:

potential (mV)=−11.25 log [NO concentration (ppm)]−13.57 log [NO$_2$ concentration (ppm)]+62.78   (2)

Furthermore, the oxygen exhausting electrode 2 and oxygen sensing electrode 3 were made to operate in a measurement gas of various NOx concentrations and an oxygen concentration of 0.5% under a temperature of 600° C. to control the oxygen concentration in the first chamber to 0.1%, a voltage was impressed across the oxygen exhausting electrodes 5, 5a to obtain a current flow of 0.05 mA, and the electromotive force of the composite sensing electrode was measured as well as the potential across the oxygen exhausting electrode 5 and the reference electrode 6. The concentrations of NO$_2$, NO in the measurement gas, the electromotive force and the potential at this time as well as the NO, NO$_2$ concentrations found from Equations (1) and (2) are as shown in Table 2.

TABLE 2

| NOx CONCENTRATION IN MEASUREMENT GAS | | EMF OF COMPOSITE SENSING ELECTRODE | POTENTIAL OF OXYGEN EXHAUSTING ELECTRODE | NOx CONCENTRATION BASED UPON SENSOR OUTPUT VALUE | |
|---|---|---|---|---|---|
| NO$_2$ (ppm) | NO (ppm) | TRODE (mV) | TRODE (mV) | NO$_2$ (ppm) | NO (ppm) |
| 20 | 80 | 25.3 | 23.8 | 19.8 | 79.6 |
| 50 | 40 | 48.3 | 21.7 | 49.9 | 40.5 |
| 80 | 50 | 60.0 | 17.9 | 79.0 | 50.2 |
| 100 | 20 | 65.8 | 21.3 | 99.6 | 18.9 |

The electromotive force at the composite sensing electrode corresponds to the NO$_2$ concentration, and the concentration of NO, which was obtained from the potential across the oxygen exhausting electrode 5 and reference electrode 6 and the concentration of NO$_2$ found by the composite sensing electrode, agrees almost precisely with the NO density in the measurement gas. Thus, by detecting two output values and processing them using a microcomputer or the like, the concentrations of NO$_2$ and NO in exhaust gas could be sensed. Thus it was confirmed that NOx concentration can be detected accurately.

Thus, the NOx sensor according to the present invention makes it possible to detect the total amount of NOx in exhaust gas as well as the concentrations of NO and NO$_2$ by a single element without oxidizing or reducing NO or NO$_2$ to effect a conversion to NO or NO$_2$ gas.

As many apparently widely different embodiments of the present invention can be made without departing from the spirit and scope thereof, it is to be understood that the invention is not limited to the specific embodiments thereof except as defined in the appended claims.

What is claimed is:

1. A method for measuring concentration of NOx in a target gas, comprising the steps of:

exposing a first electrode to the target gas and a second electrode to an atmospheric air, wherein said first and second electrodes are fixed to the same ion conductive solid electrolytic substrate;

passing a bias current between said first electrode and said second electrode using a constant-current source such that the polarization potential of said first electrode falls within a range of −0.3~0.4V (exclusive of 0V); and detecting an electromotive force generated across said first electrode and said second electrode while passing said bias current between said first electrode and said second electrode.

2. A method for measuring concentration of NOx in a target gas, comprising a step of:

exposing first and second electrodes to the target gas, wherein said first and second electrodes are fixed to the same ion conductive solid electrolytic substrate;

passing a bias current between said first electrode and said second electrode using a constant-current source such that the polarization potential of said first electrode and said second electrode falls within a range of 0.05~0.5V and −0.03~0.5V respectively; and detecting an electromotive force generated across said first electrode and said second electrode while passing said bias current between said first electrode and said second electrode.

3. A method for measuring concentration of NOx in a target gas, comprising a step of:

exposing a first electrode to the target gas and a second electrode to said target gas or an atmospheric air, wherein said first and second electrodes are fixed to the same ion conductive solid electrolytic substrate;

passing a bias current between said first electrode and a third electrode using a constant-current source such that the polarization potential of said first electrode falls within a range of −0.3~0.4V (exclusive of 0V), wherein said third electrode is fixed to the same ion conductive solid electrolytic substrate as said first and second electrodes; and detecting an electromotive force generated across said first electrode and said second electrode while passing said bias current between said first electrode and said third electrode.

4. A method for measuring concentration of NOx in a target gas, comprising a step of:

exposing first and second electrodes to the target gas, wherein said first and second electrodes are fixed to the same ion conductive solid electrolytic substrate;

passing a bias current between said first electrode and a third electrode, and said second electrode and said third electrode using a constant-current source such that the polarization potential of said first electrode and said second electrode falls within a range of 0.05~0.5V and −0.03~0.5V respectively, wherein said third electrode is fixed to the same ion conductive solid electrolytic substrate as said first and second electrodes; and detecting an electromotive force generated across said first electrode and said second electrode while passing said bias current between said first electrode and said third electrode.

* * * * *